US008858424B2

(12) United States Patent
Hasegawa et al.

(10) Patent No.: US 8,858,424 B2
(45) Date of Patent: Oct. 14, 2014

(54) ENDOSCOPIC SYSTEM FOR SURGICAL INSTRUMENT POSITION CONTROL AND POSITION CONTROL METHOD THEREOF

(75) Inventors: Jun Hasegawa, Hino (JP); Michifumi Yoshie, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1281 days.

(21) Appl. No.: 12/539,778

(22) Filed: Aug. 12, 2009

(65) Prior Publication Data

US 2009/0299136 A1    Dec. 3, 2009

Related U.S. Application Data

(63) Continuation of application No. PCT/JP2008/052441, filed on Feb. 14, 2008.

(30) Foreign Application Priority Data

Feb. 14, 2007   (JP) .................................. 2007-033824

(51) Int. Cl.
| *A61B 1/00*   | (2006.01) |
| *A61B 1/018*  | (2006.01) |
| *A61B 19/00*  | (2006.01) |
| *A61B 1/005*  | (2006.01) |
| *A61B 17/29*  | (2006.01) |
| *A61B 17/00*  | (2006.01) |
| *A61B 17/3211*| (2006.01) |
| *A61B 17/32*  | (2006.01) |

(52) U.S. Cl.
CPC ........... *A61B 17/00234* (2013.01); *A61B 17/29* (2013.01); *A61B 1/018* (2013.01); *A61B 2017/00353* (2013.01); *A61B 17/3211* (2013.01); *A61B 19/22* (2013.01); *A61B 19/5225* (2013.01); *A61B 2019/2242* (2013.01); *A61B 17/320016* (2013.01); *A61B 2019/2276* (2013.01); *A61B 1/0051* (2013.01)
USPC ............................ 600/106; 600/145; 600/146

(58) Field of Classification Search
CPC ........... A61B 1/00098; A61B 1/00133; A61B 1/0016; A61B 1/0051
USPC .................................................. 600/106, 146
See application file for complete search history.

(56) References Cited

U.S. PATENT DOCUMENTS

| 4,273,111 A  * | 6/1981  | Tsukaya ........................ 600/145 |
| 4,699,125 A  * | 10/1987 | Komatsu ....................... 600/109 |
| 6,726,675 B1 * | 4/2004  | Beyar ............................ 604/510 |
| 2005/0113640 A1 * | 5/2005 | Saadat et al. .................. 600/106 |
| 2006/0069310 A1 * | 3/2006 | Couvillon ..................... 600/148 |

FOREIGN PATENT DOCUMENTS

| JP | 3007715 | 11/1999 |
| JP | 3236070 | 9/2001  |

(Continued)

*Primary Examiner* — Alireza Nia
(74) *Attorney, Agent, or Firm* — Scully, Scott, Murphy & Presser, P.C.

(57) ABSTRACT

In an endoscopic system, when an affected area of a biomedical tissue in an image is treated with a scalpel and a holding pair of forceps which movably extend from a distal portion of an endoscope through the endoscope while the image taken by the endoscope in a body cavity in a time-series manner is being observed, a treatment is performed in which the holding pair of forceps holds the affected area detached from the biomedical tissue by the scalpel. When any motion is detected in the distal portion of the endoscope included in the image, a motion direction and a motion amount of the distal portion of the endoscope attributed to the motion are detected, and the distal portion of the endoscope is curved to return the scalpel to an original treatment position.

10 Claims, 7 Drawing Sheets

(56) References Cited

FOREIGN PATENT DOCUMENTS

| JP | 2003-127076 | 5/2003 |
| JP | 2004-135781 | 5/2004 |
| JP | 2004-141486 | 5/2004 |
| JP | 2004-194827 | 7/2004 |

* cited by examiner

ENDOSCOPIC SYSTEM FOR SURGICAL INSTRUMENT POSITION CONTROL AND POSITION CONTROL METHOD THEREOF

CROSS REFERENCE TO RELATED APPLICATIONS

This is a Continuation Application of PCT Application No. PCT/JP2008/052441, filed Feb. 14, 2008, which was published under PCT Article 21(2) in Japanese.

This application is based upon and claims the benefit of priority from prior Japanese Patent Application No. 2007-033824, filed Feb. 14, 2007, the entire contents of which are incorporated herein by reference.

BACKGROUND OF THE INVENTION

1. Field of the Invention

The present invention relates to an endoscopic system for position control of surgical instruments such as a scalpel and a forceps to be inserted through a forceps channel of an endoscopic apparatus.

2. Description of the Related Art

An endoscopic apparatus is generally known as equipment for observing, for example, a lesion in a body cavity. This endoscopic apparatus has an imaging unit which is provided at the distal portion of an insertion portion of an endoscope to be inserted into the body cavity or which is provided in the main unit of the apparatus. Thus, the endoscopic apparatus displays a desired observation target as an image on a monitor. This insertion portion is flexible, and is provided with a channel (forceps channel) penetrating from the proximal side to the distal end. A surgical instrument such as a pair of forceps or a scalpel (electric scalpel) is inserted as needed from an insertion hole of the forceps channel, so that various treatments can be administered to, for example, the lesion while endoscopic images are being observed at the same time.

Furthermore, as disclosed in, for example, Japanese Patent No. 3007715, there has recently been proposed an electrically operated endoscopic apparatus to reduce the burden on a surgeon in the operation of an endoscope. Moreover, in connection with a surgical instrument, as disclosed in, for example, Jpn. Pat. Appln. KOKAI Publication No. 2003-127076, there has been proposed an electrically operated and robotized surgical instrument not only to reduce the operational burden on the surgeon but also to reduce the burden on a patient by the reduction of the time for an operation.

In a surgery using an endoscope, a biomedical tissue (affected area) in which, for example, a lesion is generated is cut and detached by a surgical instrument inserted through a forceps channel of the endoscope. Here, the affected area is detached so that a view between a mucous membrane and a muscular coat may be secured by lifting, with a holding pair of forceps, the mucous membrane cut by a scalpel. In this case, as the held mucous membrane becomes greater along with the progress of detachment, motion in the direction of gravity or motion opposite to the direction of the lifting with the holding pair of forceps acts on the endoscope due to the increase of the weight of the mucous membrane or the increase in the amount of lifting with the holding pair of forceps. If this motion is great, the distal end of the scalpel also moves away from the position of the treatment, so that a surgeon performs the operation of returning the distal end of the scalpel to the original treatment position every time. Further, for example, Japanese Patent No. 3236070 discloses a technique for moving an endoscope in accordance with the movement of the distal end of a surgical instrument.

BRIEF SUMMARY OF THE INVENTION

According to an embodiment of the present invention, there is provided an endoscopic system for surgical instrument position control, the endoscopic system comprising: an endoscope having a curvable distal portion to observe a biomedical tissue in a body cavity; a first surgical instrument which movably extends from the distal portion of the endoscope through the endoscope and which treats the biomedical tissue; a second surgical instrument which movably extends from the distal portion of the endoscope through the endoscope and which is configured to hold a part of the biomedical tissue treated by the first surgical instrument; a motion detector which detects the motion of the distal portion of the endoscope; and a control unit which detects a motion direction and a motion amount in accordance with the result of the detection by the motion detector and which controls the curving of the distal portion of the endoscope to return the first surgical instrument to a treatment position where the first surgical instrument had been located immediately before moving.

According to another embodiment, there is provided a method of controlling the positions of first and second surgical instruments in an endoscopic system when treating a biomedical tissue in an image by use of the first and second surgical instruments which movably extend from a distal portion of an endoscope through the endoscope while observing the image taken by the endoscope in a body cavity in a time-series manner, the method comprising: performing a treatment in which the second surgical instrument holds a part of the biomedical tissue detached from this biomedical tissue by the first surgical instrument, and when any motion is detected in the distal portion of the endoscope included in the image, detecting a motion direction and a motion amount of the distal portion of the endoscope attributed to the motion, and then curving the distal portion of the endoscope to return the first surgical instrument to a treatment position where the first surgical instrument had been located immediately before moving.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described in detail with reference to the drawings.

Figure 1:
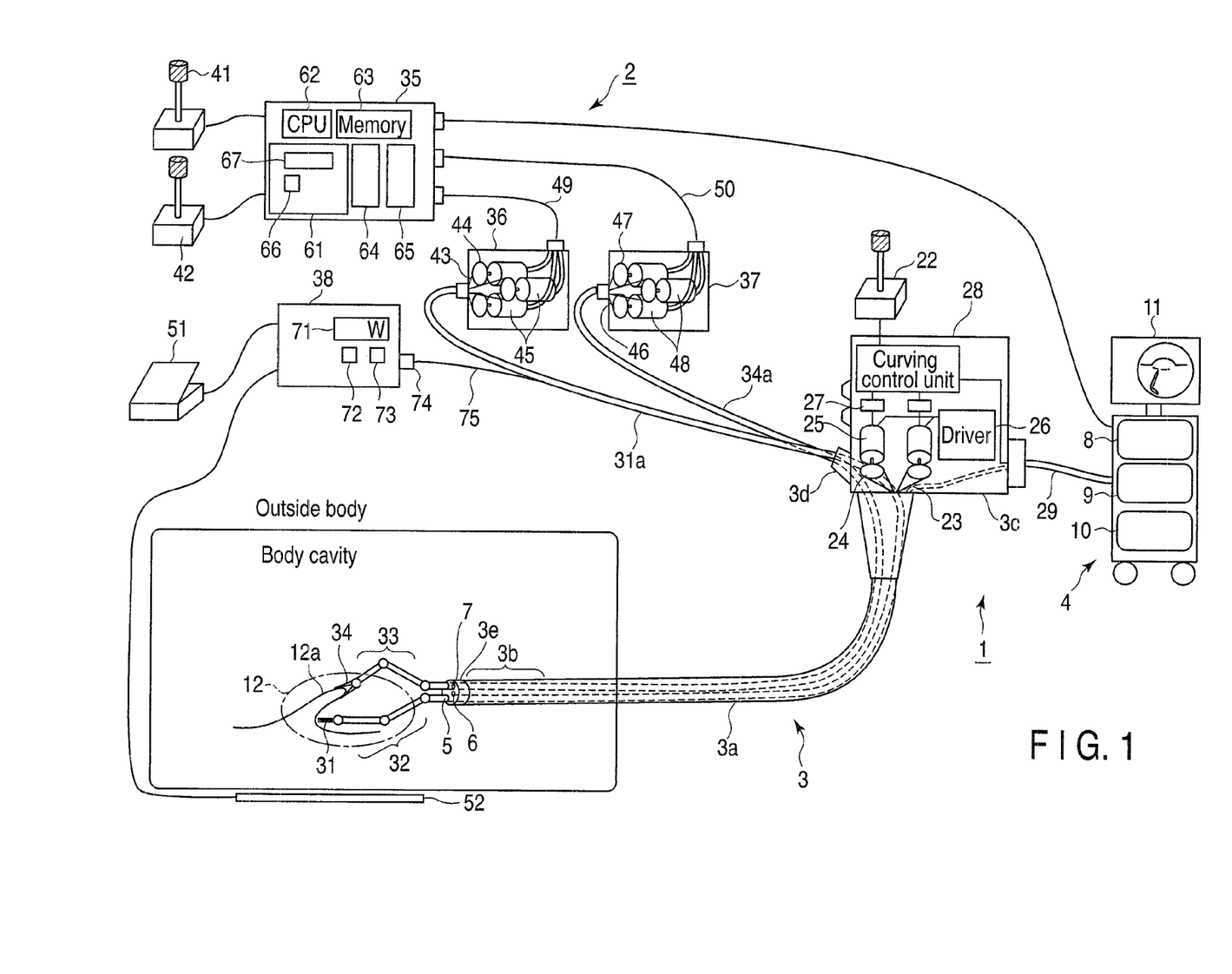
FIG. 1 is a diagram showing the overall configuration of an endoscopic system for controlling the position of a surgical instrument according to a first embodiment.

FIG. 1 is a diagram showing the overall configuration of an endoscopic system for controlling the position of a surgical instrument according to a first embodiment of the present invention.

This endoscopic system is broadly composed of an endoscopic apparatus 1 and a surgical instrument apparatus 2 equipped with two surgical instruments. The surgical instruments in the present embodiment are, by way of example, a scalpel 31 and a holding forceps 34 having multi-joint structures (which, e.g., bend and axially rotate). Each of these surgical instruments is a master-slave electric surgical instrument which activates each joint in accordance with the operation of two input devices (joysticks) 41, 42. Further, the embodiments according to the present invention can be applied to an electronic endoscope having an image pickup device provided at the distal end of an insertion portion, and to an endoscope which takes an optical image guided by a fiber scope. In the embodiments described below, the electronic endoscope is explained by way of example.

First, the endoscopic apparatus is described.

The endoscopic apparatus 1 comprises an endoscopic main unit 3 and an apparatus main unit 4. The endoscopic main unit 3 includes an insertion portion 3a to be inserted into a body cavity, and an operation portion 3c which curves a curving portion 3b provided on the distal side of the insertion portion 3a.

The insertion portion 3a is provided with, for example, a plurality of holes made on the proximal side and penetrating from an insertion opening 3d to a distal portion 3e, which are so-called forceps holes 5 in a forceps channel, and a light guide fiber 6 or the like for propagating illumination light for illuminating an observation view field. Further, the distal portion 3e is provided with an imaging unit 7 including an image pickup device such as a CCD and an optical system. Image data on a biomedical tissue including an affected area taken by the imaging unit 7 is sent, through the operation portion 3c, to a later-described image processing unit 8 of the apparatus main unit 4 connected by a cable (including a light guide fiber, an image signal line and a control signal line) 3g.

Furthermore, the operation portion 3c is an electric curving operation portion, and a joystick 22 is connected to this operation portion 3c. An operator or surgeon operates the joystick 22 to curve the curving portion 3b, and thereby brings the condition of a treatment of an affected area 12 in the biomedical tissue targeted for a treatment into the observation view field (or an image view field). This observation view field contains, as imaging subjects, the distal portions of the holding forceps 34 and the scalpel 31 described later.

The operation portion 3c includes a plurality of wires 23 connected on one end to the curving portion 3b, a plurality of pulleys 24 coupled to the other ends of the wires 23, a plurality of motors 25 having rotation shafts fitted with the pulleys 24, a driver 26 for independently driving each of the motors 25, an encoder 27 provided in each of the motors 25, and a curving control unit 28 for controlling the motor driver 26 on the basis of a value detected by the encoder 27. The encoder 27 generates a signal corresponding to a revolution, and sends the signal to the curving control unit 28 for feedback control of the motors 25.

Furthermore, the operation portion 3c is connected to the apparatus main unit 4 by a cable 29. This cable 29 includes a signal line composed of a light guide fiber for sending the illumination light, an image signal line and a control signal line.

Moreover, the apparatus main unit 4 comprises the image processing unit 8 which performs various kinds of image processing and data processing on the image data acquired by the imaging unit 7, a light source unit 9 which generates the illumination light applied to the observation view field from an illumination light window 6 through the light guide fiber, a control unit 10 which controls the whole endoscopic system and which includes a motion estimator for performing motion-related processing described later, and a monitor 11 which displays, for example, a taken image, data on this image, the state of the apparatus and operational instructions. The control unit 10 includes, as one function, the motion estimator for performing arithmetic operation to estimate the moving position and moving direction associated with the later-described motion and calculate a movement (direction and distance) for return to an original position (treatment position). Although the illumination light is sent by the light guide fiber in the configuration shown in the present embodiment, a light source such as a light emitting diode may be provided at the distal portion 3e of the endoscopic apparatus.

The surgical instrument apparatus 2 comprises a surgical instrument for treating the affected area 12 in the biomedical tissue, for example, the scalpel 31 such as a high-frequency electric scalpel attached to the distal end of a multi-joint arm 32, the holding forceps 34 which is attached to the distal end of a multi-joint arm 33 and which holds, for example, a mucous membrane detached with the scalpel 31, a surgical instrument control unit 35 for controlling the scalpel 31 and the holding forceps 34, a surgical instrument driving unit (a scalpel motor unit 36 and a forceps motor unit 37) for driving the scalpel 31 and the holding forceps 34 in accordance with a control signal of the surgical instrument control unit 35, and a power supply unit 38 for supplying high-frequency power to the scalpel 31. The joysticks 41, 42 are connected to the surgical instrument control unit 35, and these joysticks 41, 42 are input units for giving instructions for the movement and postures the scalpel 31 and the holding forceps 34 in accordance with the hand operation of the surgeon. Further, the power supply unit 38 includes a foot switch 51 for giving an instruction to apply the high-frequency power to the scalpel 31 in accordance with the foot operation of the surgeon, and a return electrode 52 which is connected to the power supply unit 38 and which is affixed to the surface of the body of a patient to be treated.

The scalpel 31 and the holding forceps 34 are coupled, via the multi-joint arms 32, 33, to retractable and flexible surgical instrument insertion portions 31a, 34a which are inserted into the forceps channel. The proximal sides of the surgical instrument insertion portions 31a, 34a are connected to the scalpel motor unit 36 and the forceps motor unit 37, respectively. Such a configuration enables the scalpel 31 and the holding forceps 34 to be three-dimensionally moved in the body cavity. In the present embodiment for example, a structure combining a plurality of joints with short and small rods is used for the multi-joint arms 32, 33. Instead of the multi-joint component, various components can be used as movable components, such as a columnar piezoelectric element. Moreover, instead of the wires, a small motor or magnetic force can be provided as a driving source to drive the joints.

The scalpel motor unit 36 includes a wire 43 connected on one end to the joints of the multi-joint arm 32 through the surgical instrument insertion portion 31a, a pulley 44 coupled to the other end of the wire 43, and a motor 45 having a rotation shaft fitted with the pulley 44. Similarly, the forceps motor unit 37 includes a wire 46 connected on one end to the joints of the multi-joint arm 33 through the surgical instrument insertion portion 34a, a pulley 47 coupled to the other end of the wire 46, and a motor 48 having a rotation shaft fitted with the pulley 47. These motors 45, 48 are connected to the surgical instrument control unit 35 by cables 49, 50, and are independently driven and controlled.

This surgical instrument control unit 35 transmits, to a motor driver 65, a control signal for driving the motors 45, 48 in accordance with the amount of operation of the joysticks 41, 42 by the surgeon, and rotates the motors 45, 48. An unshown encoder for measuring the revolution is attached to each of the motors 45, 48. The encoder generates a signal corresponding to the revolution and sends the signal to the surgical instrument control unit 35, so that feedback control of the motor 45, 48 is performed. According to this configuration, the motors 45, 48 are rotated and the joints of the multi-joint arms 32, 33 are bent by the tractional force of the wires 43, 46 wound by the pulleys 44, 47. Further, the surgical instrument insertion portion 31a, 34a are moved back and forth and rotated by unshown actuators provided in the motor units 36, 37 to rotate and move back and forth the scalpel 31, to rotate the holding forceps 34 and to move back and forth and open/close jaws.

The surgical instrument control unit 35 includes a function control input unit 61 for inputting instructions from the joysticks 41, 42 as well as function control conditions or parameters from an input portion of an unshown operation panel or the like, a central processing unit (CPU) 62 for performing various kinds of arithmetic processing and instructing the components, a memory 63 for saving images and communication data or the like, and the motor driver 65 for driving and controlling the motors 45, 48 in the motor units 36, 37. In addition, the surgical instrument control unit 35 is connected to the motor units 36, 37 and the apparatus main unit 4 by cables, and is provided with an unshown communication function (interface function) for communicating therewith.

The function control input unit 61 includes a switch 66 for switching on/off a function of fixing the positions (parts) of the scalpel 31 and the holding forceps 34, a display 67 for displaying the state of the function, an image receiver 64 for receiving, from the endoscopic main unit 3, an image taken by the imaging unit 7 at the distal end of the endoscope, and a memory 63 for storing the received image, results of arithmetic operations by the CPU 62 and the communication data.

The power supply unit 38 is provided with a display 71 for displaying, for example, the state of power supply, an output wattage input panel 72, an output mode selection panel 73, and a power output terminal 74. The power output terminal 74 supplies high-frequency power output from an internally provided power unit (not shown) to the scalpel 31 through a cable 75. This cable 75 is inserted through the surgical instrument insertion portion 31a together with the wire 43, and connected to the high-frequency electric scalpel at the distal end of the scalpel 31.

Although the joysticks are respectively provided in the endoscope and the surgical instrument in the configuration example of the present embodiment, these operation functions may be combined into one joystick.

Figure 2A:
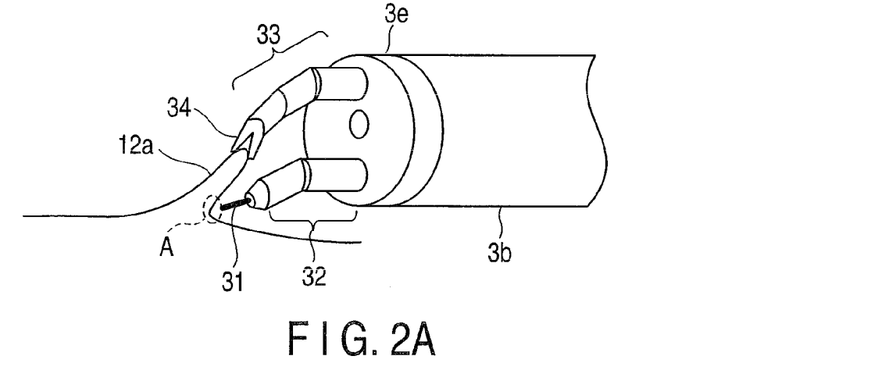
FIG. 2A is a diagram showing one example of a treatment using a scalpel and a holding pair of forceps according to the first embodiment.

In the endoscopic system equipped with the surgical instrument apparatus having such a configuration, a mucous membrane 12a cut (detached) with the scalpel 31 is lifted up by the holding pair of forceps 34 as shown in FIG. 2A to allow visibility between the mucous membrane 12a and a muscular coat (under the mucous membrane).

Figure 2B:
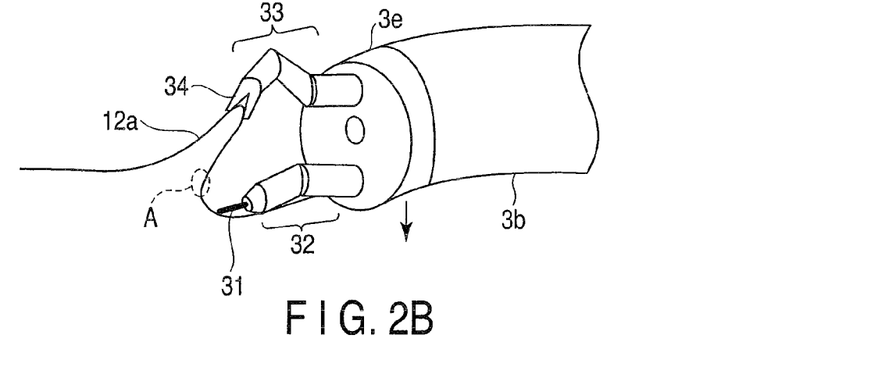
FIG. 2B is a diagram showing, following FIG. 2A, one example of the treatment using the scalpel and the holding pair of forceps according to the first embodiment.

However, the weight of the mucous membrane increases or the amount of lifting force by the holding forceps 34 increases as the mucous membrane 12a is more detached, so that the distal end of the endoscope moves from an initial treatment position A in the direction of gravity or in a direction opposite to the lifting direction of the holding forceps 34 as shown in FIG. 2B. Therefore, the distal end of the endoscope is lifted up again to return the scalpel 31 to the treatment position A.

A motion detector according to the present embodiment is mainly composed of the image processing unit 8 and the control unit 10. The motion detector detects a motion direction and a motion amount (moving distance) of the distal end of the endoscope in accordance with an image taken before the motion and an image taken after the motion.

Figure 2C:
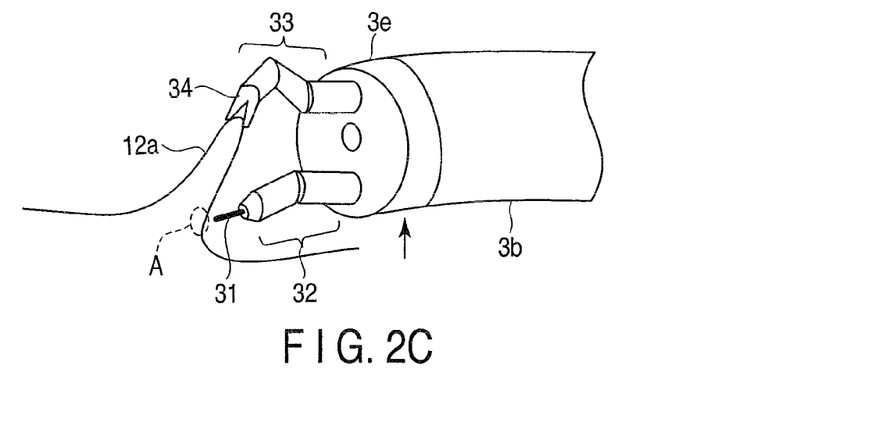
FIG. 2C is a diagram showing, following FIG. 2B, one example of the treatment using the scalpel and the holding pair of forceps according to the first embodiment.

As shown in FIG. 2C, the driver 26 is feedback-controlled by the control unit 10 serving as the motion detector in accordance with the detected motion direction and motion amount in the present embodiment. Under this control, the endoscope is curved so that the movement of the distal portion 3e of the endoscope may correspond to the motion, that is, so that the scalpel 31 may be returned to the original position (treatment position). Such a method of estimating the motion direction and distance of the distal portion of the endoscope from the images adjacent in a time-series form is known and disclosed in, for example, Japanese Patent No. 3007715.

Figure 3:
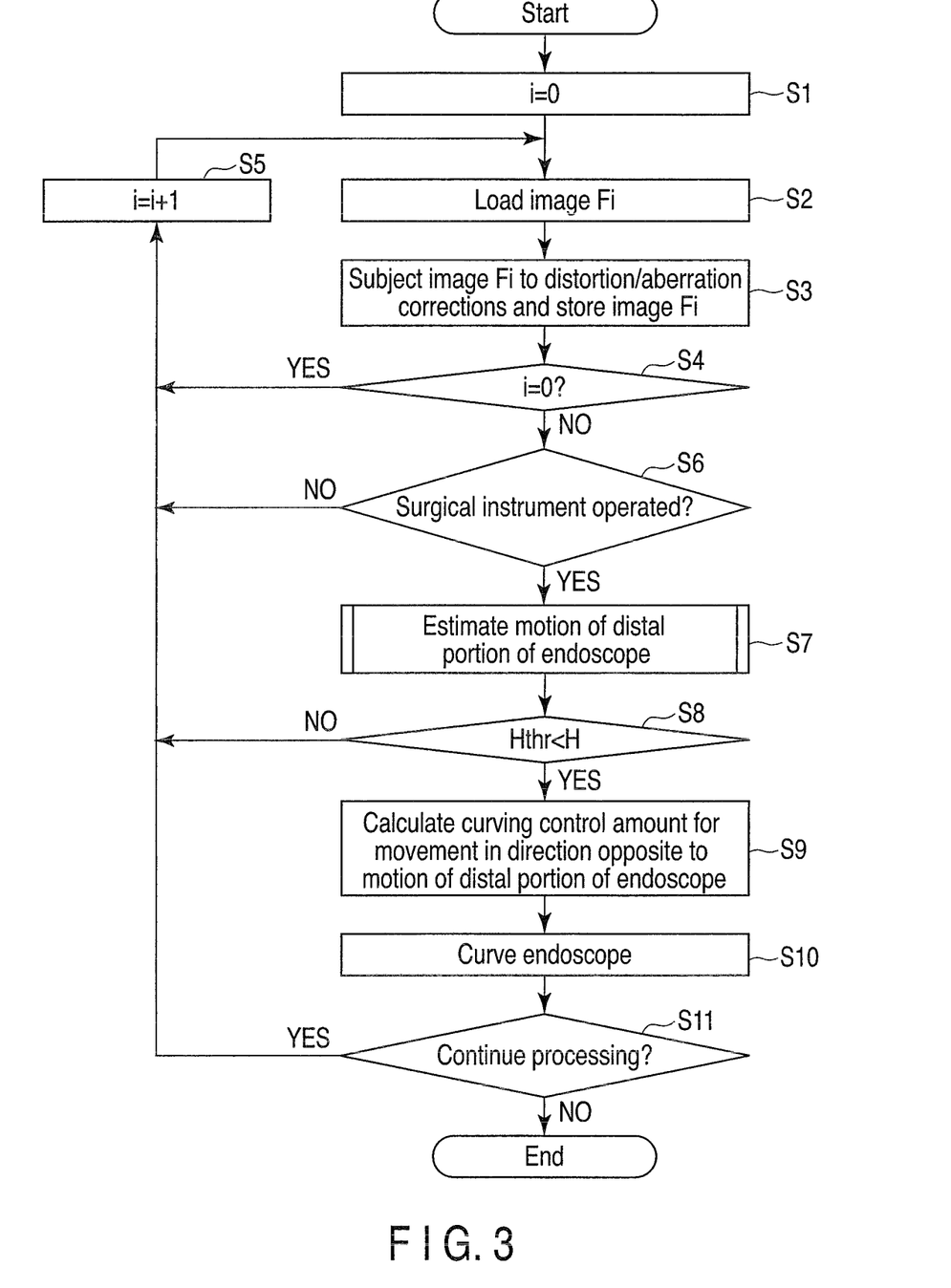
FIG. 3 is a flowchart for explaining the motion of the distal end of an endoscope and the movement for return to an original treatment position according to the first embodiment.
Figure 4:
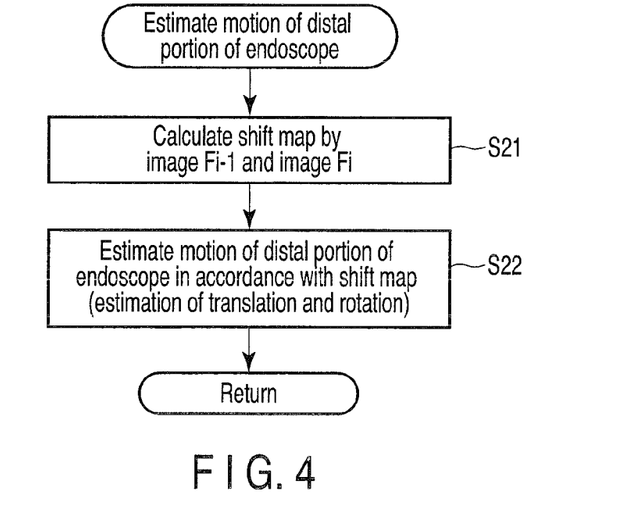
FIG. 4 is a flowchart of a subroutine for explaining the estimation of the motion of the distal portion of the endoscope.

The motion of the distal end of the endoscope and the movement back to the original treatment position are described with reference to flowcharts shown in FIGS. 3 and 4.

First, in the image processing unit 8, the number of images (image data) Fi to be taken is initialized (i=0) (step S1). The image Fi taken by the imaging unit 7 is loaded (step S2), subjected to distortion/aberration corrections, and temporarily stored in the memory 63 (step S3).

Then, whether the image is an initially loaded image F0 that is, whether the number of images i is equal to 0 is judged (step S4). If the image is judged to be the image F0 (YES), an increment (i=i+1) is made (step S5), and the flow moves to step S2 to again load the image Fi. On the other hand, if the image is not the initially loaded image F0 (NO), whether a treatment with the scalpel 31 which is the surgical instrument is performed is judged (step S6).

If it is judged in step S6 that the treatment with the scalpel 31 is not performed (NO), the distal portion 3e of the endoscope is judged to be not down, and the flow moves back to step S5 to load the next image. On the other hand, if the treatment with the scalpel 31 is performed (YES), it is judged that the distal portion 3e of the endoscope may be down, and the motion of the distal portion 3e of the endoscope is estimated (step S7). Here, the motion of the distal portion of the endoscope is described with reference to a subroutine shown in FIG. 4.

A shift map is created using a previously loaded image Fi−1 and the image Fi loaded immediately after the image Fi−1, that is, using the image before the motion and the image after the motion (step S21). That is, the motion (a translation vector and a rotational matrix R) of the endoscope with respect to a target part (e.g., the affected area 12) determined in the image is estimated by comparing the images adjacent in a time-series form. However, the translation vector is a unit vector. This estimation is disclosed in, for example, Japanese Patent No. 3347385. Although the shift map is obtained from two images adjacent in a time-series form in the present embodiment, a plurality of time-series images may be used.

Furthermore, the size k of the translation vector is calculated by a method disclosed in Jpn. Pat. Appln. KOKAI Publication No. 9-26547 (a fourth embodiment in this publication), and a translation vector H=kh is found (step S22). When the size of the translation vector H is smaller than a threshold value Hthr, it is judged that the distal end of the endoscope has not moved. Then, an increment (i=i+1) is made (step S5), and the flow moves to step S2 to again load the image Fi. On the other hand, when the size of the translation vector H is greater than the threshold value, it is judged that the distal end of the endoscope has moved, and the flow moves to step S10.

Figure 5A:
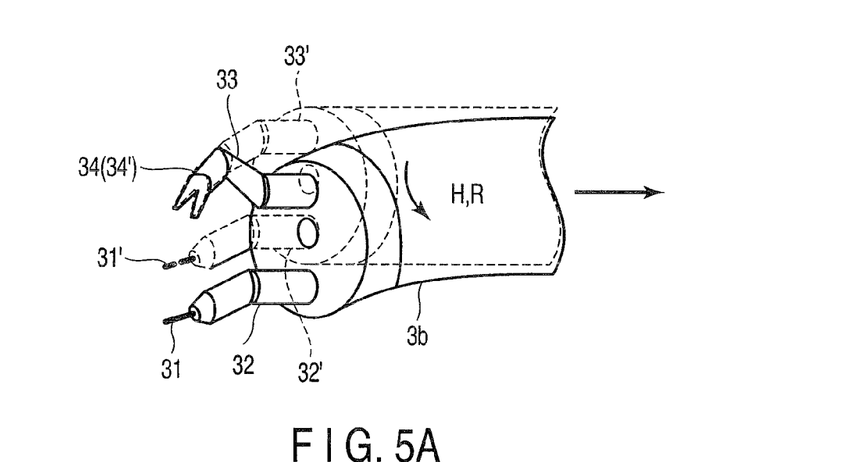
FIG. 5A is a diagram for explaining how the scalpel and the holding pair of forceps move in accordance with the motion of the distal portion of the endoscope.
Figure 5B:
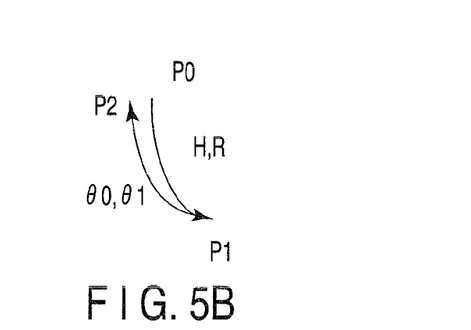
FIG. 5B is a diagram showing how the position of the distal portion of the endoscope moves.

Then, as shown in FIGS. 5A and 5B, a curving amount for curving the endoscope to return its distal end to the original position is estimated from the motion (the translation vector H and the rotational matrix R) of the distal end of the endoscope (step S9). For example, the position P0(x', y', z') of the distal end of the endoscope before the motion based on a coordinate system after the movement of the endoscope is represented by the following equation:

$$\begin{pmatrix} x' \\ y' \\ z' \end{pmatrix} = R^{-1} \begin{pmatrix} x - H_x \\ y - H_y \\ z - H_z \end{pmatrix}$$ [Equation 1]

wherein the position of the distal end of the endoscope before its motion is P0(x, y, z).

Moreover, a vertical curving amount θ0 and a horizontal curving amount θ1 of the distal portion of the endoscope are estimated as follows:

$$E = \sqrt{(x'-x'')^2 + (y'-y'')^2 + (z'-z'')^2} \rightarrow \min$$ [Equation 2]

wherein the position P2 of the distal end of the endoscope obtained by controlling the curving of the endoscope is (x", y", z"). The position of the distal end of the endoscope is returned to the position P2 as shown in FIG. 5B on the basis of the estimated curving amounts θ0, θ1 (step S10). The series of operations is repeated.

As described above, the motion of the distal portion of the endoscope is estimated using the taken images while the treatment is being performed with the scalpel 31. The curving amount for return to the original position (treatment position A: FIG. 2A) of the distal portion of the endoscope can be calculated from the estimated value, and this curving amount is used to control the movement so that the scalpel is always located at the treatment position. Moreover, if the motion of the distal portion 3e of the endoscope is small and the treatment with the scalpel 31 is continued, the operation amounts of bending, rotation and back-and-forth movement in the joints of the multi-joint arms of the scalpel 31 and the holding forceps 34 can be calculated to return the scalpel 31 to the treatment position from the position to which the scalpel has moved. Then, the joints can be activated to return the scalpel 31 to the original treatment position.

According to the endoscopic system equipped with the surgical instrument apparatus in the present embodiment described above, when the distal portion 3e of the endoscope has moved from the treatment position due to the increase of the weight of the mucous membrane in the holding forceps 34 or the increase in the amount of lifting force by the holding forceps 34 for holding the affected area 12 cut or detached out of the body cavity, the motion of the distal portion 3e of the endoscope is estimated from the images taken before and after the motion of the endoscope. From the estimated motion, the movement of the scalpel 31 back to the original position can be estimated.

Thus, the surgeon can concentrate on the treatment with the scalpel 31 and the holding forceps 34 to cut or detach the affected area without performing any position correcting operation attributed to the motion of the distal portion of the endoscope. This reduces the operational burden on the surgeon, lessens fatigue, and eliminates the interruption of the treatment due to the movement. Consequently, time required for the treatment is reduced, and the patient can feel less pain and fatigue.

Next, a second embodiment is described.

Figure 6:
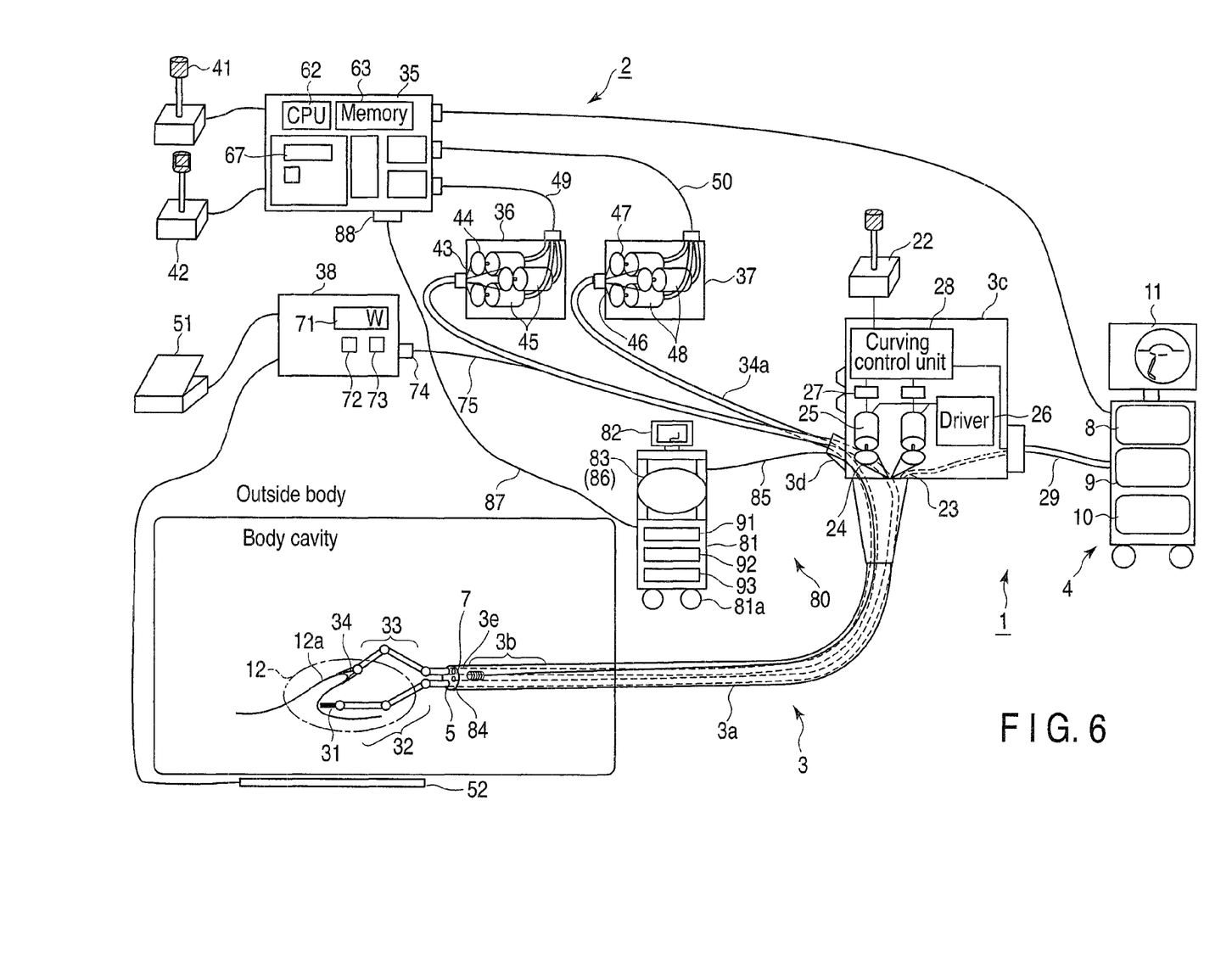
FIG. 6 is a diagram showing the overall configuration of an endoscopic system for controlling the position of a surgical instrument according to a second embodiment.

FIG. 6 is a diagram showing the overall configuration of an endoscopic system for controlling the position of a surgical instrument according to the second embodiment. In the configuration of the present embodiment, an endoscopic shape observation apparatus is added to the configuration of the endoscopic system in the first embodiment described above. In the present embodiment, components other than components in the endoscopic shape observation apparatus are equivalent to the components in the endoscopic system shown in FIG. 1, and are therefore provided with the same reference numbers and not described.

An endoscopic shape observation apparatus 80 comprises a circuit unit 81 incorporating a driving circuit 91 for a magnetic field generating coil, a detection circuit 92 for the output of the magnetic field generating coil and a position estimation/calculation circuit 93, a monitor 82, a magnetic field detection unit 83, and a magnetic field generating coil 84. At least one magnetic field generating coil 84 is provided on the distal side of a curving portion 3b of an endoscopic main unit 3, and connected, by a signal line 85, to the endoscopic shape observation apparatus 80 disposed in the vicinity of a patient (body cavity).

A magnetic field generated by the magnetic field generating coil 84 is detected by a plurality of magnetic field detection coils 86 (86a, 86b, ... 86n) provided in the magnetic field detection unit 83.

The position estimator 81 receives data, through the signal line 85, on the magnetic field detected by the magnetic field detection coils 86, and estimates the position of the magnetic field generating coil 84. However, the estimated position of the magnetic field generating coil 84 is indicated by a value on a coordinate system based on the magnetic field detection unit 83. As the position of the distal end of an endoscope when an image is taken is found by a positional relation (design value) with the magnetic field generating coil 84, the amount of motion of the distal end of the endoscope between images can be calculated. In addition, the principle of position estimation is as follows: the magnetic field generating coil is disposed at the distal end of the endoscope, a generated magnetic field is detected by the plurality of detection coils arranged outside the body, and the position and direction of the magnetic field generating coil are estimated from the detected value. The details are disclosed in Japanese Patent No. 3571675.

Figure 7:
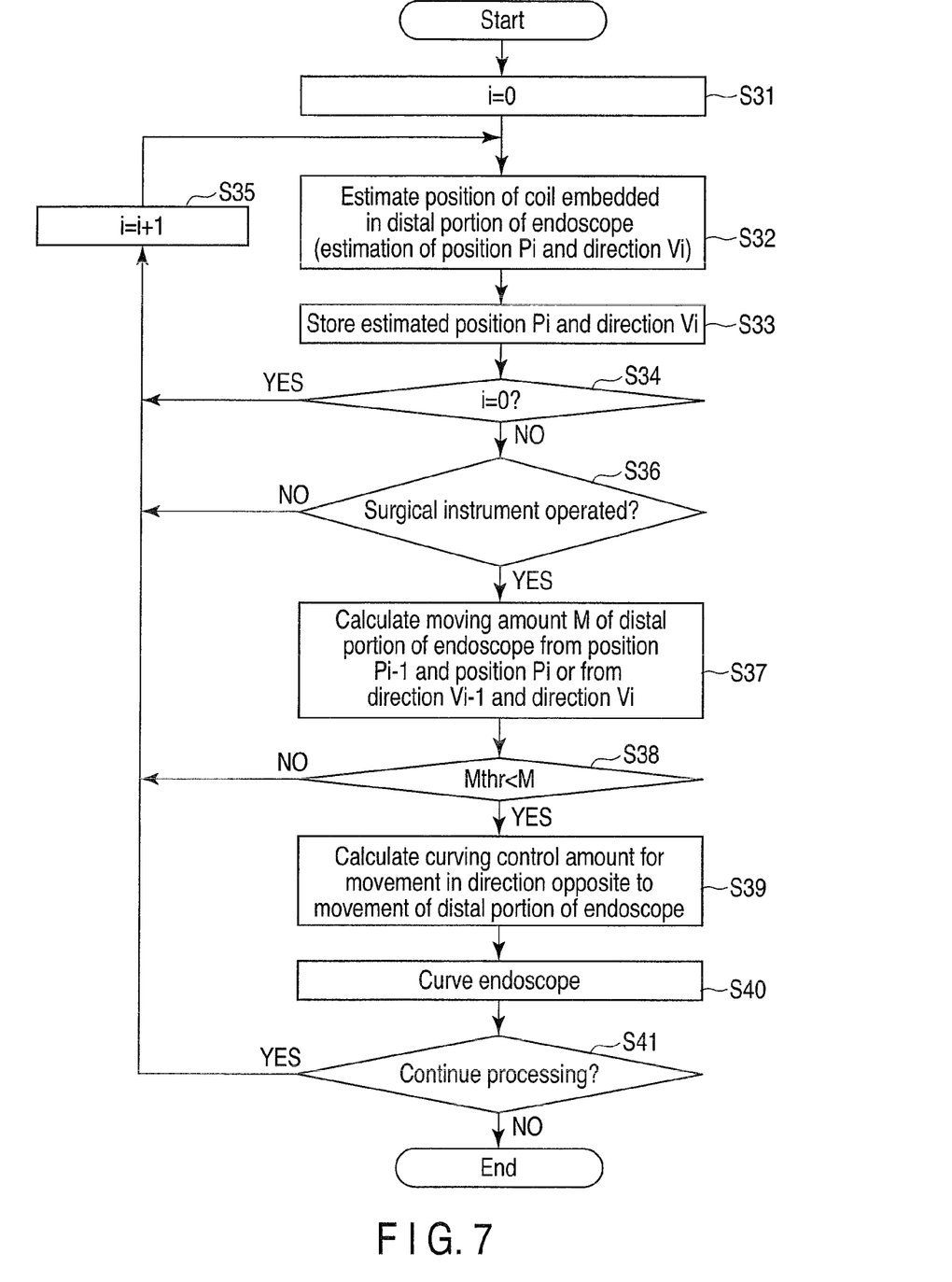
FIG. 7 is a flowchart for explaining the motion of the distal portion of an endoscope and the movement for return to an original treatment position according to the second embodiment.

The motion of the distal end of the endoscope and the movement back to an original treatment position are described with reference to a flowchart shown in FIG. 7.

First, the endoscopic shape observation apparatus 80 drives the magnetic field generating coil 84 by a driving circuit of the motion estimator 81 to generate a magnetic field. When a program for the flowchart in FIG. 7 is started, a CPU 62 of a surgical instrument control unit 35 initializes i of the position Pi and direction Vi of the distal portion of the endoscope (i=0) (step S31). When an image is taken by an image processing unit 8, the position Pi and direction Vi of the magnetic field generating coil 84 are estimated by the endoscopic shape observation apparatus 80 at the same time (step S32). The estimated position (position Pi, direction Vi) is temporarily stored in a memory (step S33). Since i is initially equal to 0, a start position (position P0, direction V0) is estimated.

Then, whether the position is the initially loaded position (position P0, direction V0), that is, whether i is equal to 0 is judged (step S34). If this position is judged to be the position (position P0, direction V0) (YES), an increment (i=i+1) is made (step S35), and the flow moves to step S32 to again estimate and store the position Pi, Vi of the distal portion of the endoscope. On the other hand, if it is judged in step S34 that the position is not the initially loaded position P0 (NO), whether a treatment with a scalpel 31 is performed is judged (step S36).

If it is judged in step S36 that the treatment with the scalpel 31 is not performed (NO), the distal portion 3e of the endoscope is judged to be not down, and the flow moves to step S35 to estimate the next position Pi, Vi of the distal portion of the endoscope. On the other hand, if the treatment with the scalpel 31 is judged to be performed (YES), a motion amount M of the distal end of the endoscope is calculated (step S37). The motion amount M of the distal end of the endoscope is calculated by comparing a previously loaded position (position Pi−1, direction Vi−1) with the position (position Pi, direction Vi) loaded immediately after the previously loaded position.

Then, whether the obtained motion amount M is greater than a preset motion amount threshold value Mthr is judged (step S38). If the motion amount M is judged to be equal to or smaller than the threshold value Mthr (NO), it is judged that the distal portion of the endoscope has not so moved as to be returned to the initial position. Then, the treatment with the scalpel 31 is continued, and the flow moves to step S35 for the next position detection.

On the other hand, if it is judged in step S38 that the motion amount M is greater than the threshold value Mthr (YES), a curving control amount is calculated to move the distal portion of the endoscope in a direction opposite to its motion to return the distal portion of the endoscope to the original treatment position (step S39). Then, the distal portion of the endoscope is curved in accordance with this curving control amount to move the distal portion of the endoscope back to the original treatment position (step S40). After this movement, whether to continue the treatment with the scalpel 31 is judged (step S41). If the treatment with the scalpel 31 is judged to be continued (YES), the flow moves back to step S35. On the other hand, if the treatment is no longer continued (NO), the driving of the magnetic field generating coil 84 is stopped, and a sequence for position detection is ended.

According to the endoscopic system equipped with the surgical instrument position controller in the second embodiment described above, the motion amount of the endoscope (the size of a translation vector) can be accurately calculated, so that the scalpel 31 and a holding forceps 34 can be more quickly moved back to the treatment position before the motion. Further, the threshold value is provided in detecting the motion of the distal portion of the endoscope, so that vibrations caused by unnecessary position holding operation for the surgical instrument due to, for example, noise or a calculation error are prevented, thereby preventing any difficulty in the treatment.

Next, a third embodiment is described.

In the present embodiment, the configuration of an endoscopic system is the same as the configuration of the endoscopic system in the first embodiment described above, and the position of a holding forceps before and after the curving operation of an endoscope is controlled. The endoscopic system in the present embodiment is equivalent to the endoscopic system shown in FIG. 1, and is therefore provided with the same reference numbers and is not described.

Figure 8A:
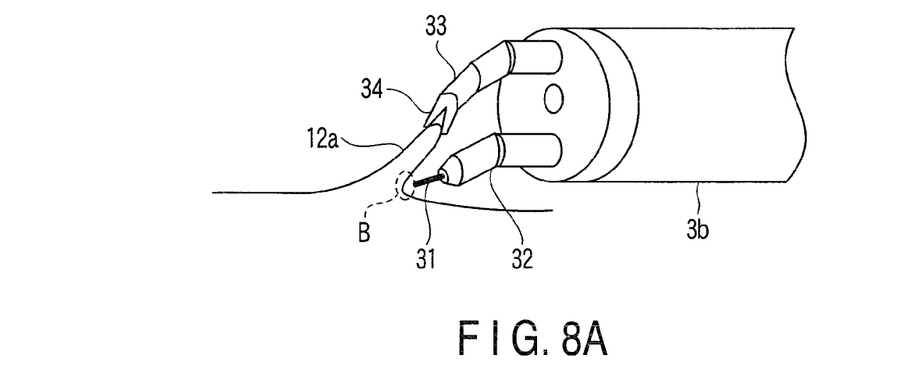
FIG. 8A is a diagram for explaining the movement of the distal end of an endoscope according to a third embodiment.
Figure 8B:
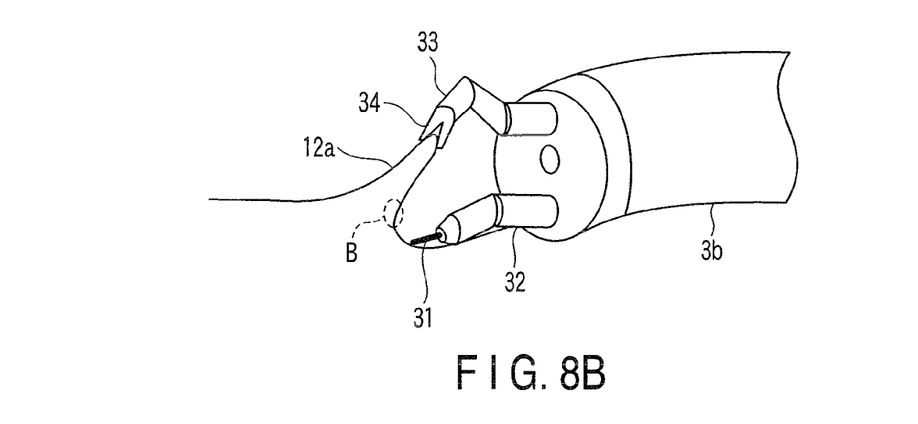
FIG. 8B is a diagram for explaining, following FIG. 8A, the movement of the distal end of the endoscope according to the third embodiment.
Figure 8C:
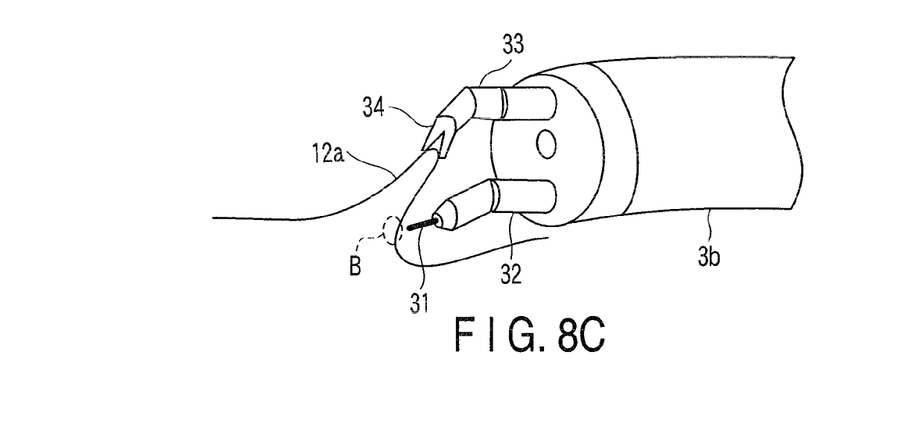
FIG. 8C is a diagram for explaining, following FIG. 8B, the movement of the distal end of the endoscope according to the third embodiment.

In the present embodiment, as shown in FIGS. 8A, 8B, 8C, a mucous membrane 12a held by a holding forceps 34 is lifted up as detached by a scalpel 31. If the distal portion of the endoscope moves in this situation, the scalpel 31 is moved back to an original treatment position B as in the embodiments described above. Here, the mucous membrane 12a held by the holding forceps 34 is also moved, that is, stretched. Therefore, depending on the degree of the stretch of the mucous membrane 12a, the detached mucous membrane 12a may deform, and an affected area may deform, or a line made so far by the cutting and detachment with the scalpel 31 may be distorted.

In the present embodiment, when the scalpel 31 is moved back to the original treatment position B, unnecessary force is prevented from being applied to the mucous membrane 12a by taking the motion of the holding forceps into account.

The position of the distal end of the holding forceps after the distal end of the endoscope has moved is calculated from the amount of rotation of a motor for the bending, back-and-forth movement and rotation of the holding forceps, and is $(x_a', y_a', z_a')$. From position coordinates $(x', y', z')$ after the distal end of the endoscope is moved by the holding forceps 34 and from position coordinates $(x'', y'', z'')$ of the distal end of the endoscope after the endoscope is curved, the motion amount of the distal end of the endoscope is:

$$(x''-x', y''-y', z''-z') \quad \text{[Equation 3]}$$

The holding forceps moves synchronously with the endoscope when the endoscope is curved, so that the position of the holding forceps after curving is $(x_a', y_a', z_a')$.

Thus, the position $(x_a'', y_a'', z_a'')$ of the holding forceps before curving after the endoscope is curved is $$\begin{pmatrix} x_a'' \\ y_a'' \\ z_a'' \end{pmatrix} = \begin{pmatrix} x_a' - (x''-x') \\ y_a' - (y''-y') \\ z_a' - (z''-z') \end{pmatrix} \quad \text{[Equation 4]}$$

The coordinate system of the holding forceps 34 is found, so that the bending and back-and-forth movement of the joints of the holding forceps, that is, the rotation amount of a corresponding motor 48 (shown in FIG. 1) is found by an inverse problem. The value of this rotation amount is used to control the motor 48 and move the holding forceps.

As described above, according to the present embodiment, the holding forceps is moved together with the movement of the endoscope to take into consideration the bending and extension of the multi-joint arms which support the holding forceps, so that unnecessary force is prevented from being applied to the mucous membrane being lifted. This makes it possible to detach the held mucous membrane without deformation. Moreover, a line made so far by the cutting or detachment with the scalpel can be preserved.

As described above, according to the endoscopic system and its position control method of the present embodiment, the motion of the distal portion of the endoscope caused by the increase of the load of a mucous membrane detached from an affected area and held during a treatment or the increase in the amount of lifting with the holding forceps is estimated. The distal portion of the endoscope is moved to the original position in accordance with the result of the estimation, whereby the position of the surgical instrument can be controlled in such a manner as to enable the treatment to be continued without any movement of the surgical instrument away from the treatment position.

What is claimed is:

1. An endoscopic system for surgical instrument position control, the endoscopic system comprising:
    an endoscope comprising a curvable distal portion to observe a biomedical tissue in a body cavity;
    a curving driver unit which generates driving force to curve the distal portion;
    a surgical unit comprising:
        a first surgical instrument which movably extends from the distal portion of the endoscope through the endoscope and which is configured to be operated to treat the biomedical tissue; and
        a second surgical instrument which movably extends from the distal portion of the endoscope through the endoscope and which is configured to hold a part of the biomedical tissue treated by the first surgical instrument;
    a motion detector configured to detect a motion direction and a motion amount of the distal portion of the endoscope between a time before movement and a time after the movement of the distal portion depending on an amount of force generated by the hold of the second surgical instrument; and
    a control unit configured to:
        determine that an operation of the surgical unit is performed,
        control, after determining that an operation of the surgical unit is performed, the motion detector to detect the motion direction and the motion amount of the distal portion of the endoscope,
        calculate, based on the detected motion direction and the detected motion amount, an amount of control to return the first surgical instrument to a treatment position where the first surgical instrument had been located immediately before moving, and
        control the curving driver unit based on the calculated amount of control to generate driving force to curve the distal portion of the endoscope to return the first surgical instrument to the treatment position where the first surgical instrument had been located immediately before moving.

2. The endoscopic system for surgical instrument position control according to claim 1, wherein the first surgical instrument and the second surgical instrument are provided at the distal end of at least one multi-joint arm which retractably and bendably extends from the distal portion of the endoscope through the endoscope.

3. The endoscopic system for surgical instrument position control according to claim 1, wherein:
    the endoscope further comprises an imaging unit;
    the motion detector comprises:
        an image processing unit which processes an image taken by the imaging unit, and
        a motion estimator which estimates a motion and moving position of the distal portion of the endoscope on the basis of image data obtained by the image processing unit; and
    images successively taken by the imaging unit in a time-series manner are sequentially compared with each other in order of time, and a motion direction and a motion amount of the distal portion of the endoscope are detected in accordance with the result of the comparison.

4. The endoscopic system for surgical instrument position control according to claim 1, wherein the motion detector includes
    a magnetic field generating coil disposed in the endoscope to be inserted into the body cavity, and
    a position estimator which detects a magnetic field generated by the magnetic field generating coil and which estimates the position and the amount of motion of the endoscope using the position of the magnetic field generating coil as coordinates.

5. The endoscopic system for surgical instrument position control according to claim 3 or 4, wherein the control unit moves the distal portion of the endoscope in a direction opposite to the motion on the basis of the motion direction and the motion amount when the motion amount detected by the motion detector exceeds a prepared threshold value.

6. The endoscopic system for surgical instrument position control according to claim 2, further comprising a treatment driver unit which generates driving force to drive the first surgical instrument and the second surgical instrument,
    wherein the control unit outputs a control signal to one of a treatment actuator and a holding actuator to drive the multi-joint arm to bend and extend in accordance with the curving of the distal portion of the endoscope so that the second surgical instrument holding the biomedical tissue maintains a holding position where the second surgical instrument is located after the motion, in the case where the distal portion of the endoscope is curved in accordance with the result of the detection by the motion detector.

7. The endoscopic system for surgical instrument position control according to claim 6, wherein an insertion portion of the endoscope, a multi-joint arm provided with the first surgical instrument and a multi-joint arm provided with the second surgical instrument are curved by the traction and relaxation of wires which are coupled to pulleys attached to shafts of motors, and perform moving operation, holding operation and posture sustaining operation by driving of the motors in accordance with an instruction from the control unit.

8. The endoscopic system for surgical instrument position control according to claim 1, wherein the control unit is configured to control the curving driver unit based on the calculated amount of control while the surgical unit is being operated.

9. The endoscopic system for surgical instrument position control according to claim 8, wherein the control unit is configured to determine that the first surgical instrument is being operated.

10. The endoscopic system for surgical instrument position control according to claim 9, wherein the control unit is configured to control the curving driver unit based on the calculated amount of control while the first surgical instrument is being operated.

* * * * *